(12) United States Patent
Silva

(10) Patent No.: US 10,675,168 B2
(45) Date of Patent: *Jun. 9, 2020

(54) ANKLE FOOT ORTHOSIS

(71) Applicant: Eugenio R Silva, Coral Gables, FL (US)

(72) Inventor: Eugenio R Silva, Coral Gables, FL (US)

(*) Notice: Subject to any disclaimer, the term of this patent is extended or adjusted under 35 U.S.C. 154(b) by 266 days.

This patent is subject to a terminal disclaimer.

(21) Appl. No.: 15/812,787

(22) Filed: Nov. 14, 2017

(65) Prior Publication Data

US 2018/0116855 A1   May 3, 2018

Related U.S. Application Data

(63) Continuation of application No. 12/822,967, filed on Jun. 24, 2010, now Pat. No. 9,849,020.

(51) Int. Cl.
*A61F 5/01* (2006.01)

(52) U.S. Cl.
CPC ................. *A61F 5/0127* (2013.01)

(58) Field of Classification Search
CPC ...... A61F 5/0111; A61F 5/0127; A61F 13/066
USPC ....................................... 602/16, 27
See application file for complete search history.

(56) References Cited

U.S. PATENT DOCUMENTS 5,486,157 A   1/1996  DiBenedetto
9,849,020 B2 * 12/2017 Silva ................. A61F 5/0127

* cited by examiner

*Primary Examiner* — Anna K Kinsaul
*Assistant Examiner* — Caitlin A Carreiro

(57) ABSTRACT

An ankle foot orthosis to be worn inside a common shoe that corrects ankle pronation by gently axially rotating and rolling the foot in the corrective direction by pulling from the shin assembly while further enhancing the corrective rolling with strategically placed posts on the medial edge of the sole. Rigidity of the foot assembly is paired with the flexibility of the shin assembly for donning a foot into the device when combined with a wide variety of common shoes. Features are also provided to A) support the longitudinal, transverse, metatarsal, and peroneal arches, thus enhancing the stability of the foot; and B) to support the plantar vault, thus enhancing the stability of the foot.

20 Claims, 3 Drawing Sheets

ANKLE FOOT ORTHOSIS

BACKGROUND OF THE INVENTION

1. Field of the Invention

The present invention relates to orthotics, and more particularly, to ankle and foot corrective and protective orthoses.

2. Description of the Related Art

Several designs for foot and ankle orthoses have been designed in the past. None of them, however, includes a device that can ergonomically correctly rotate a pronated ankle into proper position while being worn inside almost any kind party footwear by use of a multiplicity of means including, inter alia, specifically built-up areas, rigid and flexible portions, embedded reinforcements, bracing at specific points while also providing a gentle ankle rotation.

Applicant believes that the closest reference corresponds to U.S. Pat. No. 5,486,157 issued to DiBenedetto. However, it differs from the present invention because the present invention simultaneously rotates a pronated ankle while providing multiple built-up areas under the sole that combine to correct foot and ankle posture while still retaining the ability to flex at the ankle joint and the present invention can fit inside almost any commercially available standard footwear.

Furthermore, DiBenedetto uses right angles and brute force to straighten the ankle-foot joint where the present invention tends to counter the foot's tendency to pronate by, among other means, corrective rotation, targeted support and strategic build-ups (build up or build-ups are sometimes referred to interchangeably with post) to more naturally, and thus comfortably, improve alignment.

Other patents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide an ankle and foot orthosis that effectively corrects foot pronation or prevents further deformation in more severe cases.

It is a key object of the present invention to ergonomically and gently correct foot pronation through a variety of means including rotation, multiple built-up portions of the sole, bracing and proper supportive areas while still retaining dorsi and plantar flexion of the ankle.

It is another object of this invention to provide an orthosis that fits inside standard footwear.

Another object of the present invention is to provide an orthosis that does not require padding which can prematurely wear, add unnecessary bulk and require frequent cleaning.

It is still another object of the present invention to provide a device that is easy to adjust and remains comfortable. Specific areas are heat moldable to adjust for bony prominences and arthitic exostoses.

It is yet another object of this invention to provide such a device that is inexpensive to manufacture and maintain while retaining its effectiveness.

Further, objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawers in which.

DETAILED DESCRIPTION OF THE PREFERRED EMBODIMENT

Figure 1:
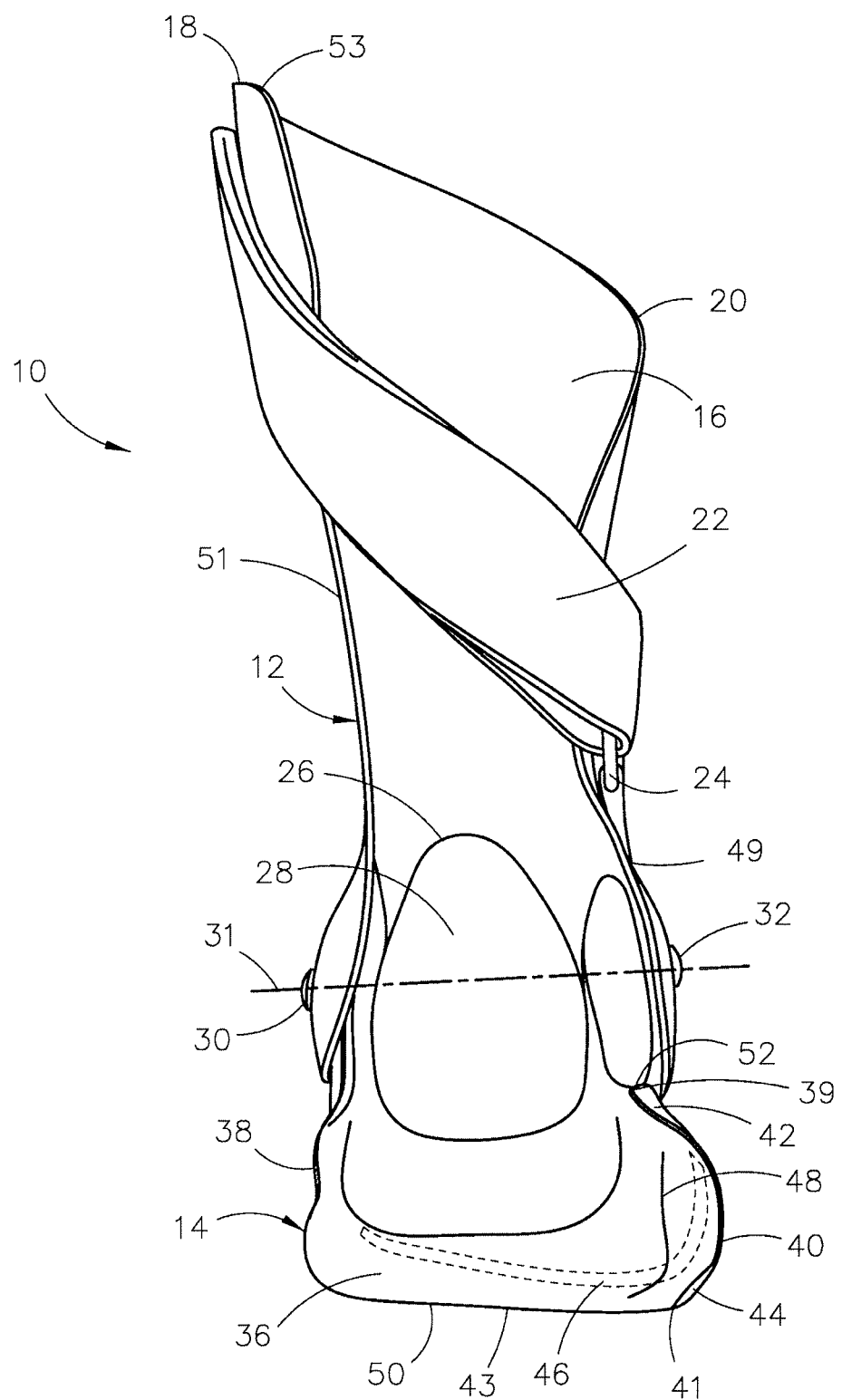
FIG. 1 represents a front perspective view of the device fitted for a right human foot.

When a balanced and healthy foot is ambulating, and is in a state of weight bearing, the foot experiences external rotation of the leg relative to that foot. This causes it to rotate upon the subtalar joint and the calcaneus goes from valgus to varus. This causes the subtalar traverse joints to go from a parallel axis to one of being incongruent and the foot then supinates. That foot transforms from an accommodative posture into a rigid lever arm capable of transmitting the force of the gastroc soleus muscles onto the ground. This process occurs from mid-stance through 'toe-off'.

At heel strike, the internal rotation of the leg relative to the foot allows the foot to rotate on the subtalar joint causing the calcaneus to go into valgus. The transverse subtalar joints become parallel and the foot becomes more accommodative to the ground by everting. This process occurs until midstance. Then the foot gradually stiffens again through 'toe-off'.

Excessive adult pronation results from the collapse of the plantar vault due to weakness of muscles and ligaments, primarily due to insufficiency of the posterior tibial tendon and the peroneus longus. When weight is applied to the foot, the medial arch collapses and a valgus deformity results. This is primarily due to two factors:

The posterior tibialis tendon, the primary inverter of the foot, attempts to ally the forces on the ligamentus structures and becomes overwhelmed and inflamed. The transverse and medial arches are lowered. the forefoot rotates medially along its long axis. The whole plantar surface of the foot contacts the ground. The forefoot rays rotate internally while the forefoot displaces laterally. As the pronation increases, the lateral everters go slack and spasm. They undergo adaptive shortening and also become painful and tender.

When the protective muscular action is overwhelmed ligaments become sprained. Joint capsules become stressed. The joints that are strained separate slightly. The foot undergoes functional deformity and that deformity become permanent. Arthritic exostoses can form and normal range of motion become affected.

The calcaneus turns on its long axis in the direction of pronation and lies flat on its medial surface. The interosseous talocalcaneal ligament becomes hypermobile and inflamed. In severe cases the angle between the Achilles tendon and the calcaneus can exceed twenty degrees. Hypolaxity of the Achilles tendon is also associated with excessive pronation.

These cases can display three distinct projections along the medial margin of the foot.

Excessively prominent medial malleolus;

Exposed medial head of the talus;

Exposed tubercle of the navicular.

These areas are sensitive to pressure and in severe cases contain exostoses.

Foot orthotics attempt to correct the pronation by bringing up the ground below the longitudinal arch. The weight bearing is increased and in very mild cases when the foot is flexible, this is tolerated; although, the medial aspect of the foot is not designed to be weight bearing surface. It does not contain fat pads. The goal of the foot orthosis is to supinate the foot by raising the longitudinal arch to an apex about the navicular.

The orthoses may be prefabricated or custom molded. It is most tolerated when a symmetrical surface to the plantar aspect of the treated foot is formed when it would be in a state of supination. If the pronation is too severe for this type of intervention one may employ ankle foot orthosis.

Most ankle foot orthoses concentrate a media-lateral compressive force concentrated on the ankle and rearfoot. Many do not permit dorsi or plantar flexion. Those that do, don't address axial forces along the long axis of foot. The forefoot is always ignored. Limiting dorsi and plantar flexion eliminates the second rocker of the foot and a compensatory gait follows. The joints above and below the ankle become over utilized.

The devices that do have ankle joints and ignore the axial forces especially the internal rotation of the forefoot, increase pressures along the prominent medial midfoot bones and are soon rejected due to the formation of excessive pressure points in that area.

Excessive pronation in the foot causes internal tibial rotation relative to the femur. The patella femoral joint is vulnerable to axial forces. It deviates laterally causing chondromalacia. Internal tibial rotation defeats the action of the cruciate ligaments and slackens the collateral knee ligaments. The result is an unstable knee joint and possible formation of a genuvalgus.

The present brace limits pronation with a comprehensive approach. Calcaneal valgus is reduced by means of a well molded foot plate and deep heelcup. Pronation is controlled by a three point pressure system consisting of a stable proximal lateral upright terminating at the apex of the most lateral aspect of the leg. This is high enough to lessen the terminal pressure to a tolerable level about the proximal third. A flexible lower and anterior medial flange is deformable to allow for ease in donning. It is then deformed axially by a proximo-lateral oriented strap that slightly inverts the foot by lifting the medial aspect of the rearfoot. It also externally de-rotates the tibia. This action unloads the talocalcaneal joint enough to relive pain while resisting the leg bones' tendency to migrate anterior-medially relative to the foot. The most distal point of support consists of a rigid flange which hugs the medial surface of the first ray between its head and base. It does not allow that ray to roll medially nor migrate anteriorly. This thin yet rigid structure allows the elimination of excessive pressure around and below the medial mid foot; the hypersensitive area where the longitudinal arch was once found and now may contain exostoses. Eversion is controlled by means of a varus forefoot posting of approximately three-sixteenths of an inch (but may range from zero to three-quarters of an inch) in height. The lateral wall prevents the forefoot from migrating laterally and also aids in supporting the transverse metatarsal arch by preventing the splay of the metatarsals.

Referring now to the drawings, where the present invention is generally referred to with numeral 10, it can be observed that it basically includes a shin assembly 12 and a foot assembly.

The shin assembly 12 is further comprised of, inter alia, a calf 16, a crest 18, an upper edge 20, a strip 22, a buckle 24, a heel edge 26 and a fastener 56. The shin assembly 12 and foot assembly 14 are connected at a first hinge 30 and a second hinge 32 resulting in an opening 28.

Figure 2:
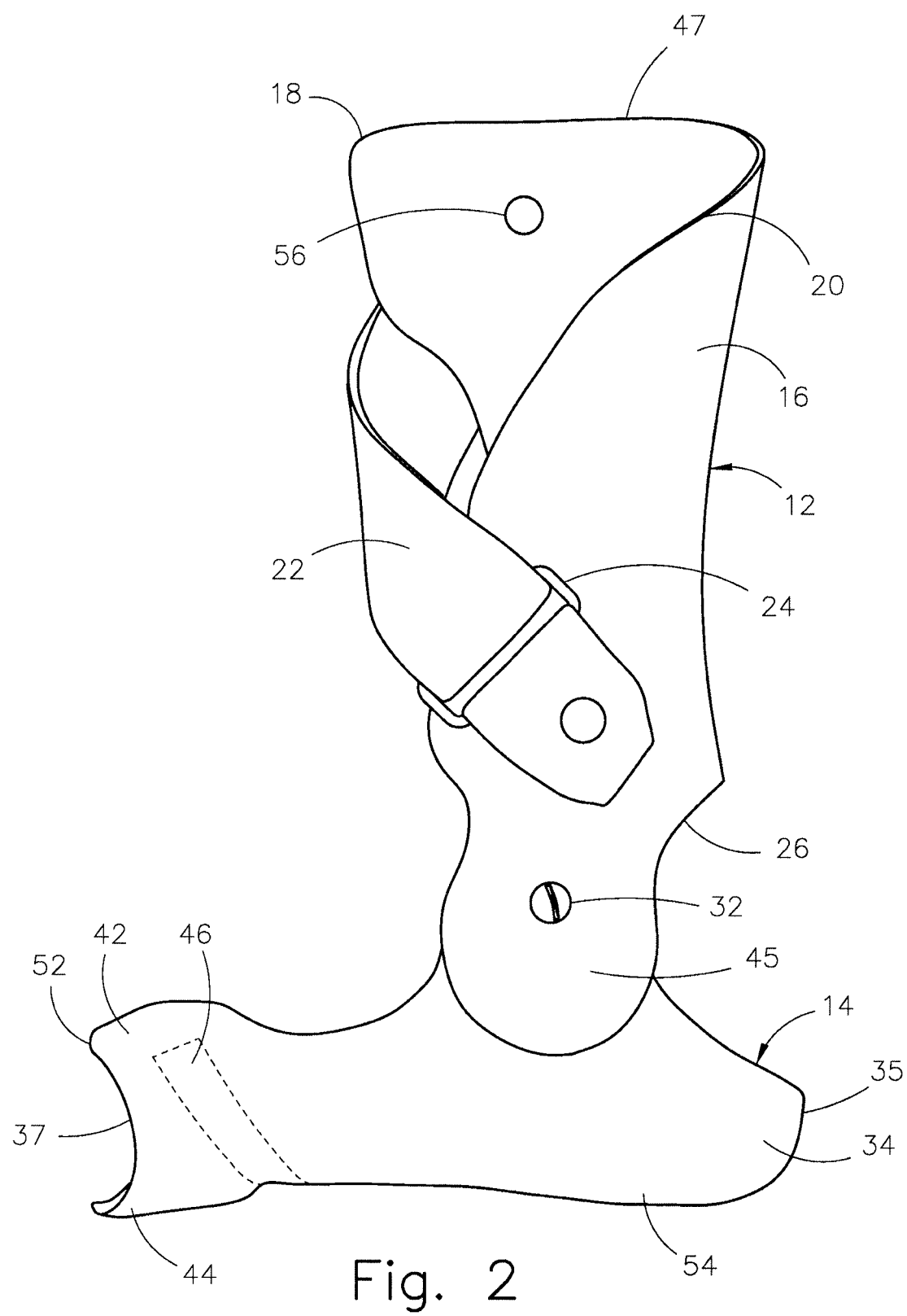
FIG. 2 shows a left side perspective view of a similar device as shown in FIG. 1.

The foot assembly 14 is further comprised of, inter alia, a heel cup 34, a sole 36, an outside edge 38, a medical edge 40, a rollover 42, a buildup 44, a reinforcement 46, an arch 48, a leading edge 50, a terminal edge 52 and a buildup 54 (shown on FIG. 2).

Figure 3:
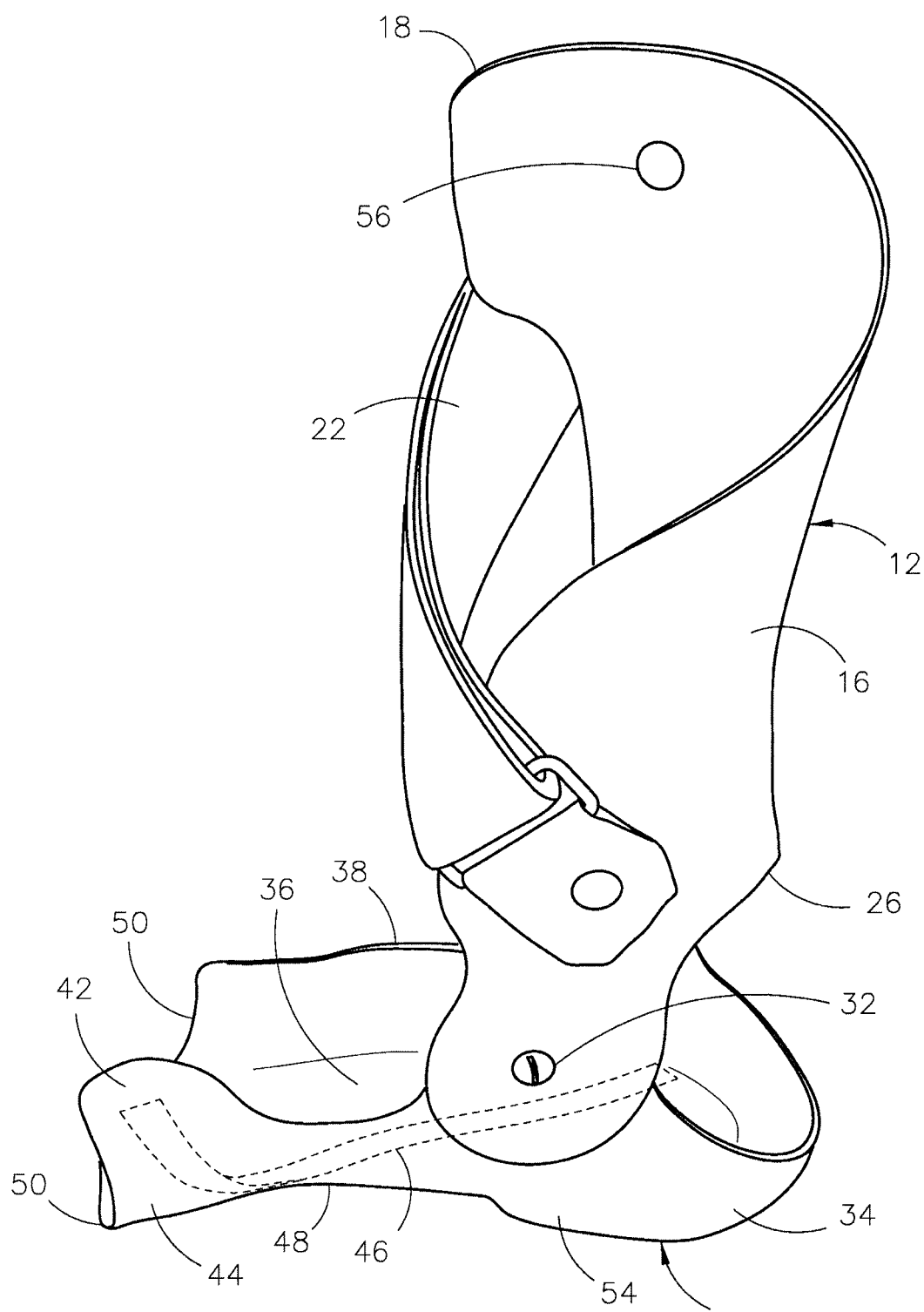
FIG. 3 illustrates an alternate left side perspective view of a similar device to that shown in FIG. 1.

Generally, FIGS. 1 through 3 demonstrate a similar preferred embodiment of the claimed ankle foot orthosis from various angles to fully describe how to make and use the device the orthosis shown in the drawings is fitted for the right food of a person and it should be appreciated that a minor image of the device shown would be appropriate for use on a person's left foot.

A key feature of the present device is that it is particularly suited for regular use only when used inside a shoe. The dimensions and construction of the device allow nearly any type of footwear to be successfully used over the device. With dimensions sufficiently slender to fit inside a shoe then a gripping means under the sole 36 is preferably absent The device is not intended to be walked on without a shoe. The device uses external footwear to effectively bind the foot into the foot assembly 14 portion of the device. The wearer's lower leg is bound into the shin assembly 12 by means of the strap 22. Each of the first hinge 30 and the second hinge 32 are preferably located outside the shoe to permit fluid dorsi and plantar flexion of the ankle.

The strap 22 is preferably separable at the buckle 24 so that the strap 22 does not impede donning a foot into the device. Once the foot is seated into the foot assembly 14 and the lower leg is in the shin assembly 12 then the strap 22 can be applied through the buckle 22 and secured. The strap 22 can be secured by any of a variety of commonly available means, such as, securing to itself with hook and loop fasteners, a belt-type buckle, laces, cam buckle or similar means that can removably secure the strap 22 in place to ensure that the lower leg is securely fastened to the shin assembly In a preferred variation the shin assembly 12 is constructed of a synthetic polymer composite such as fiberglass, plastic, multi-part resin, metal or metal alloy or combination with any of these. An important characteristic of the skin assembly 12 is that vertically it remains erect and laterally is rigid yet retains the ability on the medial leading edge to flex around the hold onto the lower leg securely when the strap 22 is tightened around the lower leg. The trough-like geometry of the shin assembly 12 naturally lends itself to rigidity in the vertical axis while retaining some flexibility to bend over the lower leg to secure it into the device. This encourages an external rotatory moment on the lower leg which is essential in resisting pronation of the foot. In a preferred variation the foot assembly 14 is constructed of a synthetic polymer composition such as fiberglass, plastic, multi-part resin, metal or metal alloy or combination of any of these. The foot assembly is preferably rigid and inflexible in all axes except for the middle medial edge. To further stiffen the foot assembly 14 a reinforcement 46 strap may be embedded into the sole 36 material from the outside lateral edge of the heel cup 34 area, through the sole 36 terminating in the rollover 42 at the first metatarsal. This reinforcement 46 particularly serves to stiffen and keep the sole 36 and rollover 42 firmly in position relative to each other. This is an important feature because if the flange deflects then pressure will be borne in the area of the medial malleolus, talus and navicular which is intolerable.

Preferably to aid in creating a comfortable device, the medial edge 40 and terminal edge 52 of the rollover 42 do not extend distal to the head of the ray of the first metatarsal and no more proximal than the base of the first metatarsal; in other words between the two prominences of the first metatarsal. It then rolls vertically terminating just medial to the extensor hallicus longus tendon on the dorsum of the foot in order not to impede upon its function or apply pressure upon it. This provides sufficient corrective roll support yet avoids creating pressure points where the device interfaces with the tendon insertion site of the first metatarsal phalangeal joint.

The sole 36 becomes thinner and ultimately to a point at the edge 50 so that a foot on the sole 36 smoothly and comfortably transitions into a shoe. If the leading edge 50 had much thickness it would essentially create an uncomfortable gap where the leading edge 50 terminates at the foot's transition into the shoe. The leading edge 50 continues under the first metatarsal ray where a buildup 44 is present to slightly pick up the first metatarsal and gently externally rotate it laterally up against the outside edge 38. The leading edge 50 terminates medially at the roller 42. The rollover 42 is present to spread out the pressure exerted onto the first metatarsal when gently rotated by the buildup 44 and arch 48. Like the edge 50, the edges of the rollover 42 are thin to minimize the surface disparity between the interior of the shoe and the foot assembly 14. This increases the comfort while wearing the device.

The buildup 44 continues toward the heel cup 34 along the medial edge of the sole 36 where it presents in another buildup comprising the transverse arch 48. The buildup under the arch 48 also tends to slightly raise the medial aspect of the foot thereby gently rolling it away from the horizontal ground. It should be appreciated by one reasonably familiar with the art of orthotics that the term buildup is often interchanged with the term post.

The lateral outside edge 38 acts to contain the foot inside the 36 and prevent unwanted lateral movement of the foot over the sole 36. By placing the foot assembly 14 portion inside a shoe, the foot is properly constrained inside the foot assembly 14. The shoe, although not an element of the claimed invention, does provide additional critical support and therefore the invention cannot be fully used without the addition of any of a wide variety of common shoes.

The line of progression is generally defined as the projected path of movement of the body's center of mass while ambulating. The normal axis of movement while ambulating of a healthy ankle joint is often not parallel to or coincidental to the line of progression. Many people's feet point slightly lateral from the path of movement.

While ambulating, healthy ankle joints typically dorsiflex or plantar flex as viewed from the sagittal plane, in an angle, from between zero and twenty-six degrees offset from the line of progression. In other words a healthy ankle joint can normally function with the toe end of the foot further away from the centerline of the body than the heel end of the foot. A common offset of ankle movement relative to the line of progression is about twenty degrees.

The first hinge 30 and second hinge 32 are the principal points of connection between the shin assembly 12 and the foot assembly 14. The first hinge 30 and second hinge 32 are positioned on opposite sides of the ankle so that they both hinge in concert. The first hinge 30 and second hinge 32 permit the foot assembly 14, and therefore necessarily the foot, to hinge on a mediolateral, horizontal axis with movement in the sagittal plane between zero and about twenty-six degrees offset from the line of progression.

Generally, the first hinge 30 and second hinge 32 are positioned over the apex of the malleoli on both sides of the ankle. Preferably but optionally the interior aspects of the hinges 30 and 32 are padded to improve contact and provide medial lateral support while still being comfortable. In other variations the interior of the first hinge 30 and second hinge 32 are cupped over the malleoli to further increase comfort and support.

In an important variation, the invention is intended to be pre-made to specifically fit a single individual. The offset of the first hinge 30 and second hinge 32 orientation relative to the line of progression is different for different people and may vary at progressive points of corrective orthotic treatment. For retail side fitting of the device, any of a series of pre-shaped shin assemblies 12 could be paired with any of a series of pre-shaped foot assemblies 14 to achieve the proper hinge axis of rotation as well as for different sized feet and complications.

The shin assembly 12 has on the upper edge 20 a crest 18 at or near the apex of the peroneus longus muscle at the superior lateral edge of the shin assembly 12. The upper edge 20\ of the shin assembly 12 spirals down to the medial aspect of shin assembly staying distal and posterior to the gastrocnemius or calf muscle to increase comport to the wearer. This spiral configuration of the upper edge 20 helps direct the external rotary force imparted by the strap 22 in the proper direction.

The posterior opening 28 formed between the intersection of the shin assembly 12 with the foot assembly 14 exposes the tendon calcaneus or Achilles tendon at the heel so that it can contact the interior of the shoe worn over the device so that the shoe grasps it and it may flex and be worn normally. The heel edge 26 preferably exposes enough of the foot so that the device is not in between the back of the shoe and the tendon calcaneus or Achilles tendon.

To use the device, the person typically wears a common sock on the foot. The strap 22 is loosened so that the heel of the foot may be seated into the heel cup 34 and the first metatarsal is supped by the rollover 42. The strap 22 is then secured over the front of the shin so that the device then moves in synchronicity with the foot. The foot and device is then inserted into a common' shoe that is laced and ties to complete securing the device to the user. The foot assembly 14 is specifically dimensioned to be able to fit inside a wide variety of footwear. In some cases the insole of the shoe may have to be removed. By minimizing the profile of the leading edge 50 and the edge 52 on the rollover 41, the foot assembly 14 perfectly transitions to the interior of the shoe making the device comfortable to sear for extended periods.

Some portions of the foot assembly and/or the shin assembly may be constructed of a heat moldable material for an increased custom fit. The generally available material softens when; heated, for example with a heat gun or upon submersion in heated water, and can be adjusted to contour an individual foot. When the material cools it solidifies into the desired shape.

A preferred embodiment is described as a leg and foot orthosis for use inside a shoe comprising a foot assembly and a shin assembly; said foot assembly is attached to said shin assembly with a first hinge immediately distal to the apex of the medial malleolus and a second hinge on or about the apex of the lateral malleolus thereby permitting a single axis, being horizontal axis 31 of movement of the shin assembly relative the foot assembly at a predetermined angle relative to the line of progression. Said foot assembly has a heel cup at a first end 35 dimensioned to fit a predetermined sized heel and a sole extending to a second end 37 as far as about a quarter inch proximal to the metatarsal heads and having a medial aspect and a lateral aspect. The foot assembly has a flange (this flange is alternatively referred to as the rollover 42) partially covering and impeding a medial axial rotation of a first metatarsal that does not extend distal to the head of the first metatarsal and no more proximal than the base of the first metatarsal on a dorsal aspect terminating before contacting the extensor halicus longus tendon and on a ventral aspect 39 integrating with said sole thereby effectively containing and preventing all five metatarsals from splaying apart and not allowing the foot to pronate or roll medially between said flange and a lateral edge 41 of the foot assembly.

The sole has a post at predetermined areas under the first metatarsal building up the medial five metatarsals from splaying apart and not allowing the foot to pronate or roll medially between said flange and a lateral edge 41 of the foot assembly. The sole has a post at predetermined areas under the first metatarsal building up the medial aspect. The sole has a post a predetermined areas under said heel cup building up the medial aspect. The foot assembly has a post a distal plantar edge 43 to provide support for the transverse metatarsal arch. The shin assembly has a distal end 45 opposite a proximal end 47 and a medial edge 49 opposite a lateral edge 51. The Sin assembly is open at the distal end so that contact with the Achilles tendon is avoided. The shin assembly is dimensioned so that the proximal lateral edge 53 extends to a predetermined point between the superior neck and the fibula and a point one third the length of the fibula from the distal end of the fibula. The superior lateral edge (sometimes referred to as the proximal lateral edge 53) of the shin assembly spirals posteriorly from said superior lateral edge, remaining distal to the gastrocnemius muscle, terminating at a flange on superior medial edge (sometimes referred to as the proximal medial edge) of the shin assembly immediately superior to the medial malleolus. The shin assembly includes an adjustable strap anchored at a first end near the superior lateral edge of the shin assembly and spirals distally to and anchors at a second end to said flange on the superior medial edge of the shin assembly such that when said strap is secured the shin assembly securely holds the lower leg and creates a force to cause external rotation of the leg against the foot.

In a variation the ankle foot orthosis may be further characterized in that said predetermined angle relative to the line of progression is between 0 to 26 degrees from the line of progression.

In yet another variation of the ankle foot orthosis it may be further characterized in that a rigid reinforcement member is integrated into the sole of the foot assembly from the ray of the first metatarsal to the lateral anklejoint.

A method for fitting any of the ankle foot orthosis as described herein selecting any foot assembly of a predetermined set of incrementally sized foot assemblies and attaching said foot assembly to a hinge to any shin assembly of a set of incrementally sized shin assemblies.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

The invention claimed is:

1. A leg and foot orthosis which reduces pronation, for use inside a shoe, the leg and foot orthosis being configured to be customized for an individual user, the leg and foot orthosis comprising:

a foot assembly and a shin assembly;

the foot assembly being attached to the shin assembly with a first hinge configured to attach immediately distal to an apex of a medial malleolus and a second hinge configured to cover an apex of a lateral malleolus, wherein the first and second hinge each create an axis which is horizontal and provides a single axis of movement of the shin assembly relative the foot assembly;

the foot assembly having a rigid heel cup which limits pronation and a sole configured to extend to a distal end about a quarter inch proximal to each metatarsal head of a user and is configured to cover the back of the heel just below the Achilles tendon of a user for whom the orthosis has been configured for;

a rigid flange configured on the medial aspect of the foot assembly wherein the rigid flange is configured to curve over the top of the first metatarsal of a user for whom the orthosis has been configured, with upwardly extending side edges configured to partially cover and impede a medial axial rotation of a first metatarsal without creating pressure points, wherein each side edge of the rigid flange terminates upwardly at a rollover configured at the first metatarsal, and wherein the rigid flange with upwardly extending side edges configured on the medial aspect is configured to not extend distal to a head of the first metatarsal and no more proximal than a base of the first metatarsal; wherein the rigid flange is configured to end over the dorsal aspect of the first metatarsal before contacting an extensor halicus longus tendon and on a ventral aspect is configured to be integrating with said sole;

a lateral side edge configured on the lateral aspect of the foot assembly to extend ventrally to the height of the fifth metatarsal and is configured to terminate before the head of the fifth metatarsal of a user for whom the orthosis is configured; wherein a combination of both upwardly extending side edges of the foot assembly are configured to effectively contain and prevent all five metatarsals of a user for whom the orthosis is configured from splaying apart and not allowing the foot to pronate or roll medially;

the foot assembly includes a reinforcing member configured to extend from a lateral aspect of the heel cup diagonally across the sole and curving upwardly onto the rigid flange to terminate at a ventral end of the rigid flange;

the foot assembly having a first buildup configured to be under a first metatarsal of a user for whom the orthosis is configured, building up the medial aspect, and configured to pick up the first metatarsal and gently rotate the first metatarsal laterally;

the shin assembly being dimensioned so that the proximal end of the lateral edge is configured to terminate between a superior neck of a fibula to a point approximately one third of the fibula length distal to the superior neck of the fibula of a user for whom the orthosis is configured;

the proximal end at the lateral edge of the shin assembly spirals posteriorly from said proximal end at the lateral edge, and is configured to remain distal to a gastrocnemius muscle, terminating at a flange on the proximal end at the medial edge of the shin assembly and configured to terminate immediately superior to a medial malleolus of a user for whom the orthosis is configured;

wherein the shin assembly includes an adjustable strap anchored at a first end near the proximal end of the lateral edge of the shin assembly and spirals distally to and anchors at a second end to said flange on the proximal end at the medial edge of the shin assembly wherein the strap is secured to the shin assembly and is configured to securely hold a lower leg in position and create a force to cause external rotation of the lower leg against the foot of a user for whom the orthosis is configured.

2. A leg and foot orthosis as described in claim 1, further comprising the foot assembly, configured below the heel cup and on the medial aspect has a second buildup configured to keep the orthosis from rolling inwardly toward the medial aspect and stabilizes the orthosis.

3. A leg and foot orthosis as described in claim 2, further comprising the foot assembly having a third buildup at a distal plantar edge which is configured to support a transverse metatarsal arch of a user for whom the orthosis is configured.

4. A leg and foot orthosis as described in claim 3, further comprising the shin assembly having a distal end opposite a proximal end and a medial edge opposite a lateral edge.

5. A leg and foot orthosis as described in claim 3, further comprising the shin assembly having a distal end opposite a proximal end and a medial edge opposite a lateral edge.

6. A leg and foot orthosis as described in claim 2, further comprising the foot assembly having a third buildup at a distal plantar edge which is configured to support a transverse metatarsal arch of a user for whom the orthosis is configured.

7. An ankle foot orthosis as described in claim 1, wherein the axis created by the hinges is characterized by a predetermined angle relative to a line of progression that is between 0 and 26 degrees from the line of progression.

8. An ankle foot orthosis as described in claim 1, wherein the foot assembly and said shin assembly contain carbon fiber.

9. A leg and foot orthosis as described in claim 1, further comprising the reinforcing member being constructed of any of a fiberglass, a multi-part resin, or a carbon fiber.

10. A leg and foot orthosis as described in claim 1, further comprising areas that are heat moldable, wherein the orthosis is configured to be customizable to correspond to a user's unique anatomy.

11. A leg and foot orthosis as described in claim 1, wherein the heel cup extends upwardly from the sole and is configured to extend continuously around the heel and completely surround the heel of a user for whom the orthosis is configured.

12. A leg and foot orthosis as described in claim 1, further comprising the shin assembly being open at the distal end so that the shin assembly is configured so as to not prevent contact between a shoe and a whole Achilles tendon.

13. An ankle foot orthosis as described in claim 1, wherein the axis created by the hinges is characterized by a predetermined angle relative to a line of progression that is between 0 and 26 degrees from the line of progression.

14. An ankle foot orthosis as described in claim 1, wherein the foot assembly and said shin assembly contain carbon fiber.

15. A leg and foot orthosis as described in claim 1, further comprising the reinforcing member being constructed of any of a fiberglass, a multi-part resin, or a carbon fiber.

16. A leg and foot orthosis as described in claim 1, further comprising areas that are heat moldable, wherein the orthosis is configured to be customizable to correspond to a user's unique anatomy.

17. A leg and foot orthosis as described in claim 1, wherein the heel cup extends upwardly from the sole and is configured to extend continuously around the heel and completely surround the heel of a user for whom the orthosis is configured.

18. A leg and foot orthosis as described in claim 1, further comprising the foot assembly, configured below the heel cup and on the medial aspect has a second buildup configured to keep the orthosis from rolling inwardly toward the medial aspect of a user for whom the orthosis is configured and stabilizes the orthosis.

19. A leg and foot orthosis as described in claim 1, further comprising the shin assembly being open at the distal end so that the shin assembly is configured so as to not prevent contact between a shoe and a whole Achilles tendon of a user for whom the orthosis is configured.

20. A leg and foot orthosis which reduces pronation, for use inside a shoe, the leg and foot orthosis being configured to be customized for an individual user, the leg and foot orthosis comprising:

a foot assembly and a shin assembly;

the foot assembly being attached to the shin assembly with a first hinge and a second hinge, wherein the first and second hinge each create an axis which is horizontal and provides a single axis of movement of the shin assembly relative the foot assembly;

the foot assembly having a rigid heel cup which limits pronation and a sole configured to extend to a distal end about a quarter inch proximal to each metatarsal head of a user and is configured to cover the back of the heel just below the Achilles tendon of a user for whom the orthosis is configured;

a rigid flange configured on the medial aspect of the foot assembly wherein the rigid flange is configured to curve over the top of the first metatarsal with upwardly extending side edges configured to partially cover and impede a medial axial rotation of a first metatarsal without creating pressure points, wherein each side edge of the rigid flange terminates upwardly at a rollover configured at the first metatarsal of a user for whom the orthosis is configured, and wherein the rigid flange with upwardly extending side edges configured on the medial aspect is configured to not extend distal to a head of the first metatarsal and no more proximal than a base of the first metatarsal; wherein the rigid flange is configured to end over the dorsal aspect of the first metatarsal before contacting an extensor halicus longus tendon and on a ventral aspect is configured to be integrating with said sole;

a lateral side edge configured on the lateral aspect of the foot assembly to extend ventrally to the height of the fifth metatarsal and is configured to terminate before the head of the fifth metatarsal; wherein a combination of both upwardly extending side edges of the foot assembly are configured to effectively contain and prevent all five metatarsals from splaying apart and not allowing the foot of a user for whom the orthosis is configured to pronate or roll medially;

the foot assembly includes a reinforcing member configured to extend from a lateral aspect of the heel cup diagonally across the sole and curving upwardly onto the rigid flange to terminate at a ventral end of the rigid flange;

the foot assembly having a first buildup configured to be under a first metatarsal, building up the medial aspect, and configured to pick up the first metatarsal and gently rotate the first metatarsal laterally;

the shin assembly being dimensioned so that the proximal end of the lateral edge is figured to terminate between a superior neck of a fibula to a point approximately one third of the fibula length distal to the superior neck of the fibula of a user for whom the orthosis is configured;

the proximal end at the lateral edge of the shin assembly spirals posteriorly from said proximal end at the lateral edge, and is configured to remain distal to a gastrocnemius muscle, terminating at a flange on the proximal end at the medial edge of the shin assembly and configured to terminate immediately superior to a medial malleolus of a user for whom the orthosis is configured;

wherein the shin assembly includes an adjustable strap anchored at a first end near the proximal end of the lateral edge of the shin assembly and spirals distally to and anchors at a second end to said flange on the proximal end at the medial edge of the shin assembly wherein the strap is secured to the shin assembly and is configured to securely hold a lower leg in position and create a force to cause external rotation of the lower leg against the foot of a user for whom the orthosis is configured.

* * * * *